(12) United States Patent
Ma et al.

(10) Patent No.: US 11,738,185 B2
(45) Date of Patent: Aug. 29, 2023

(54) IN-PLANE METAL MICRONEEDLE ARRAY AND MANUFACTURING METHOD THEREFOR

(71) Applicant: DALIAN UNIVERSITY OF TECHNOLOGY, Liaoning (CN)

(72) Inventors: Guojun Ma, Liaoning (CN); Chengwei Wu, Liaoning (CN); Yuting Niu, Liaoning (CN); Wei Zhang, Liaoning (CN); Yongtao Lv, Liaoning (CN); Xiao Han, Liaoning (CN); Jianli Ma, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 650 days.

(21) Appl. No.: 16/960,169

(22) PCT Filed: May 13, 2019

(86) PCT No.: PCT/CN2019/086662
§ 371 (c)(1),
(2) Date: Jul. 6, 2020

(87) PCT Pub. No.: WO2020/227895
PCT Pub. Date: Nov. 19, 2020

(65) Prior Publication Data
US 2021/0138215 A1    May 13, 2021

(51) Int. Cl.
*A61M 37/00*    (2006.01)
*B21G 1/00*    (2006.01)
(52) U.S. Cl.
CPC ......... *A61M 37/0015* (2013.01); *B21G 1/003* (2013.01); *A61M 2037/0053* (2013.01)

(58) Field of Classification Search
CPC ...... A61M 37/0015; A61M 2037/0053; A61M 2037/0046; A61M 2205/0244; B21G 1/003; B23H 7/02
See application file for complete search history.

(56) References Cited

U.S. PATENT DOCUMENTS 7,497,980 B2 *    3/2009    Xu ..................... B29C 33/3878
264/219

FOREIGN PATENT DOCUMENTS

CN    106512199 A    3/2017
KR    10-0682534 B1    2/2007

* cited by examiner

*Primary Examiner* — Amber R Stiles
(74) *Attorney, Agent, or Firm* — Muncy, Geissler, Olds & Lowe, P.C.

(57) ABSTRACT

An in-plane metal microneedle array and a manufacturing method therefor is disclosed. A large-size metal sheet is cut into small metal sheets. Inner sides of the upper and the lower cover plates of the tooling are provided with grooves matched with the sizes of the small metal sheets. Through holes are formed at edges around the cover plates. The metal sheets are placed in the grooves and fastened through bolts. The geometry and the size of a sheet microneedle array are designed, and a CAD model of the plane microneedles is built. A wire path is cut according to the CAD model. A few materials are reserved on both sides of substrates of the microneedle array without cutting. The unprocessed parts on both sides of the microneedle substrate are cut to obtain an in-plane metal microneedle array with a plurality of microneedle bodies.

4 Claims, 4 Drawing Sheets

IN-PLANE METAL MICRONEEDLE ARRAY AND MANUFACTURING METHOD THEREFOR

TECHNICAL FIELD

The present invention belongs to the technical field of medical apparatuses and the field of machining, and relates to an in-plane metal microneedle array and a manufacturing method therefor.

BACKGROUND

Oral administration of drugs, hypodermic administration of drugs and transdermal drug delivery are three administration modes most commonly used currently. However, oral administration of drugs needs to pass through the gastrointestinal tract and liver and other tissues and organs. Intestinal inactivation and liver "first pass effect" cause some drugs to be metabolized and the absorption efficiency is greatly reduced. On the other hand, some drugs may cause side effects such as uncomfortable stimulation to the stomach and intestines, which limits the application range of oral administration of drugs and is particularly unsuitable for the delivery of drugs such as proteins, insulin and DNA. Although the technology of hypodermic administration of drugs overcomes the above defects, inserting large-sized ordinary hypodermic needles into human tissues often causes nonnegligible pain to patients. In the process of drug delivery for infants, the pain may even lead to the failure of drug delivery, and the large-sized hypodermic needles cause greater invasiveness to human bodies, and improper handling may easily cause adverse effects such as skin infections. Thus, professionals are required for operation. In addition, ordinary hypodermic administration of drugs is to inject the drugs into the human bodies in short time, so that the local drug concentration is too high, and then the drug concentration drops rapidly, which is not conducive to continuous and stable release of the drugs for long time. The technology of transdermal drug delivery can overcome the above defects of oral administration of drugs and hypodermic administration of drugs. The transdermal drug delivery refers to a drug delivery method that applies the drugs directly to the skin surface to absorb the drugs through the subcutaneous capillaries into the human blood circulation and achieve effective blood drug concentration to achieve disease treatment or defense.

Compared with oral administration of drugs and hypodermic administration of drugs, transdermal drug delivery has the following advantages: (1) it avoids the damaging effects of the liver and the gastrointestinal tract on the drugs and improves the bioavailability of the drugs; (2) it has a slow-release effect on the drugs and can achieve long-term and controllable administration of the drugs; (3) the blood drug level is stable, which improves the therapeutic effect of the drugs; (4) it avoids the stimulation effect on the gastrointestinal tract and reduces the toxic and side effects of the drugs; (5) it can achieve painless, non-invasive or minimally invasive administration of the drugs; (6) it is simple and convenient to use, and does not need professionals for operation. Because of the advantages, the technology of transdermal drug delivery attracts extensive attention of researchers in China and abroad. However, the technology of transdermal drug delivery also has the disadvantages of small drug delivery dose, relatively low drug delivery efficiency and limited drug delivery varieties. The reason is mainly because the outermost layer of the skin has thickness of about 10-20 microns, and the stratum corneum formed by dead skin cells seriously hinders the transdermal drug penetration. In order to improve the efficiency of transdermal drug delivery and expand the types of transdermal drug delivery, people continue to research improvement methods of the technology of transdermal drug delivery from the aspects of chemistry, physics and biology, such as chemical methods using various penetration enhancers, and physical methods such as iontophoresis, ultrasonic introduction, electroporation, micropowder supersonic injection. In recent years, with the rapid development of the modern micro/nano processing technology, a novel method of promoting transdermal drug delivery which is called as a microneedle has attracted more and more attention.

The microneedle (MN) generally refers to a miniature needle with a length of tens of microns to a few millimeters and a tip diameter of tens of microns or less. As mentioned above, the barrier effect of the stratum corneum of the skin is a key problem that limits the technology of transdermal drug delivery. The microneedle is used to locally destroy the stratum corneum of the skin and form a micron-level drug delivery microchannel temporarily on the surface layer of the skin (one order of magnitude larger than the general drug molecular size), which not only significantly improves the transdermal drug delivery efficiency, but also significantly increases the application scope of the drugs for transdermal drug delivery. In addition, because the size of the microneedle is very small, the microneedle can only pierce the stratum corneum of the skin without nerves and basically does not touch the deep skin tissue which is rich in nerves and blood vessels. The pain and trauma caused by the inserting process are much smaller than those of the traditional hypodermic administration of drugs, thereby achieving painless, non-invasive or minimally invasive administration of the drugs. If combined with other microfluidic control systems, the microneedle can also achieve long-term and controllable administration of the drugs. After special design, combined with corresponding microfluidic control and analysis systems, the microneedle can also be used for painless micro biochemical analysis of the human bodies. Therefore, the related research of the microneedle has become one of the hot research directions in the medical field.

At present, domestic and foreign microneedles mainly include silicon microneedles, glass microneedles, ceramic microneedles, metal microneedles, hydrogel microneedles, polymer microneedles and sugars (such as maltose, lactose, and the like). In the microneedles, silicon is often used as microneedle material because the corresponding photolithography, dry etching, wet etching and other processing technologies are relatively mature and the material has high hardness and is easy to insert into the skin. However, during processing, the silicon microneedles have high requirements for environmental cleanliness, low processing efficiency and high corresponding cost, and thus cannot meet the requirements of batch production. In addition, the silicon, as a typical brittle material, is easy to fracture and damage if designed unreasonably, defective in processing or largely stressed during use. Moreover, because the silicon has poor biocompatibility, the fragments in the skin after fracture of the silicon may cause adverse reactions. In severe cases, the small fragments may also enter the blood vessels and heart, causing some worse consequences. Brittle materials such as glass and ceramics have similar problems. A polymer generally has better biocompatibility and toughness, and is used to manufacture the microneedles. On one hand, the rejection reaction of the body can be reduced; and on the other hand, it can ensure that the microneedle inserts into the skin without fracturing and destroying. However, because the hardness and the stiffness of polymer material are generally low, a needle tip is easy to buckle and damage in the process of inserting into the skin or human tissues, causing a failure to pierce the skin. Thus, the application is also limited. In comparison, the metal microneedles have good toughness and high strength. Moreover, the biological safety of metal such as stainless steel and titanium alloy has been verified for long time. Thus, the metal is considered as one of the preferred materials for the microneedles. At present, the processing means of the metal microneedles are very rich, including chemical etching, ultraviolet lithography, micro-milling, laser cutting, electroplating, and the like. However, the processing methods have the disadvantages of low processing accuracy, low processing efficiency and high cost, and are difficult to meet the requirements of batch production.

SUMMARY

In view of the problems in the existing manufacture technology of microneedles, the present invention provides a sheet in-plane metal microneedle array and a new processing method therefor. The plane microneedle array is made of sheet stainless steel or titanium alloy material with good biocompatibility and excellent strength and toughness, and is prepared by a traditional wire cutting processing technology. The microneedle array is composed of a substrate 6 and a microneedle body 7 for subsequent clamping assembling. The substrate and the microneedle body form a whole and are in the same plane. This type of microneedle array is easy to use. The processing method can ensure accuracy, and is suitable for high-efficiency and low-cost batch production.

To achieve the above purpose, the present invention adopts the following technical solution:

A manufacturing method for an in-plane metal microneedle array comprises the following steps:

Step 1: cutting a large-size metal sheet into small metal sheets 5 convenient for clamping, wherein the thickness of the small metal sheets 5 is 20-200 microns, the length is 30-50 mm, and the width is 10-30 mm.

Step 2: processing a special sheet clamping tooling.

The tooling is composed of two identical upper and lower metal cover plates 2, and the overall thickness of each cover plate is 5-10 mm. Inner walls of the upper and the lower cover plates of the tooling are processed with grooves 3 matched with the sizes of the small metal sheets 5, i.e., the lengths and widths of the grooves are consistent with the lengths and widths of the metal sheets 5 to place the metal sheets 5; the depths of the grooves of the upper and the lower cover plates are 1-5 mm; through holes 1 for passing through fastening bolts 4 are processed at edges around the upper and the lower cover plate bodies 2. The clamping tooling is made of metal material such as stainless steel and 45 # steel with good electrical conductivity and high strength.

Step 3: placing the small metal sheets 5 in the groove 3 of any tooling metal cover plate for stacking; adjusting the number of the metal sheets 5 placed at one time according to the thickness of the sheets and the depth of the groove; placing another tooling metal cover plate on the cover plate on which the metal sheets are placed, with the groove facing the metal sheets and aligned up and down; encapsulating the upper and the lower metal cover plates of the clamping tool by the fastening bolts 4, and compacting the metal sheets 5 to form a whole with the upper and the lower cover plates.

Step 4: designing the geometry and size of a sheet microneedle array.

The sheet microneedle array is composed of substrates 6 and microneedle bodies 7 for a subsequent clamping part, which are formed by integrally cutting the same metal sheet 5. The number of the microneedle bodies 7 on each substrate is 3-50, a distance between the microneedle bodies 7 is 0.25-10 mm, and the thickness is the thickness of the metal sheet 5. The shape of each microneedle body 7 is triangular or ensiform, the height is 100-500 microns, the width of a root of each microneedle body is 50-300 microns, and the thickness is the thickness of the metal sheet 5.

Step 5: clamping the metal sheets 5 and the tooling encapsulated in step 3 to a wire cutting device, determining a wire path according to the microneedle geometry and size designed in step 4 by the wire cutting device, conducting wire cutting on the tooling and the metal sheets 5 as a whole, and processing the metal sheets 5 into the substrates 6 and the microneedle bodies 7. In the wire cutting process, the tips of the microneedle bodies 7 are cut with an "8"-shaped path to ensure the sharpness of microneedle tips. During processing, the substrates 6 are not completely cut, and both sides are reserved for 2 to 5 mm without cutting to ensure that the tooling metal cover plates and the metal sheets 5 are still of a whole structure after cutting, thereby not only preventing the microneedles from being washed away by cooling liquid during processing, but also ensuring that the used tooling still has sufficiently high structural rigidity so that the tooling can be reused.

Step 6: taking off the fastening bolts 4 on the tooling, and taking out and washing the processed metal sheets 5.

Step 7: cutting the material on regions reserved on both sides of the substrates 6 on the metal sheets 5 in step 6 to separate the sheet microneedle array from the metal sheets 5 to obtain a sheet in-plane metal microneedle array with a plurality of microneedle bodies; and further assembling the plane microneedle array into three-dimensional microneedle arrays (out-of-plane microneedle array) with different arrangement specifications for use in design.

An in-plane metal microneedle array is provided. The sheet microneedle array is composed of substrates 6 and microneedle bodies 7. The substrates 6 and the microneedle bodies 7 are formed by integrally cutting the same metal sheet. The substrates 6 and the microneedle bodies 7 are in the same plane and the microneedle bodies 7 are located above the substrates 6, and the number, shapes and sizes of the microneedle bodies 7 are adjusted as needed. The material of the metal sheets comprises medical stainless steel or titanium alloy material. The height of the microneedle bodies 7 is 100-500 microns, the width of a root is 50-300 microns, and the thickness is the thickness of the metal sheet 5. The number of the microneedles on each substrate is 3-50, a distance is 0.25-10 mm, and the shape of each microneedle body is triangular or ensiform.

Compared with the prior art, the present invention has the beneficial effects that:

(1) The design of the sheet plane microneedles is conducive to simplifying the processing procedure, and the sheet plane microneedles are flexible to use, and can be simply assembled into three-dimensional microneedle arrays of different specifications. The metal microneedle arrays can be processed in batches at one time. Through calculation based on the ideal total cutting thickness of 2 cm for wire cutting, for example, the up-down overall wall thickness of the tooling is 5 mm, the depth of the grooves is 2 mm and the thickness of each metal sheet is 100 microns. Then, the number of the microneedles that can be cut at one time is 140, which greatly improves the efficiency compared with other microneedle processing methods. Moreover, the wire cutting processing technology has relatively low cost. Thus, the microneedle array processing method provided by the present invention has low cost.

(2) After the clamping tool is used, except that the material at the path of a cutting wire is cut off, other parts are still intact. In one aspect, it can ensure that the tooling has sufficiently high rigidity for subsequent repeated clamping; and in another aspect, because the tooling material at the processing path has been cut off, only the metal sheet needs to be cut in subsequent use, thereby further increasing the number of the metal microneedles that can be processed at one time, improving the efficiency and reducing the cost.

(3) The clamping tooling compacts the sheets into a whole, which can prevent processing size deviations caused by a lateral force during cutting. If a single metal sheet is cut, the microneedles may be deformed by a small lateral force due to small thickness, and it is difficult to ensure the processing accuracy. The microneedle tips are cut with an "8"-shaped processing path, which can effectively avoid tip passivation caused by direct direction change of the tips, thereby ensuring the processing accuracy of the microneedle tips.

Figure 1:
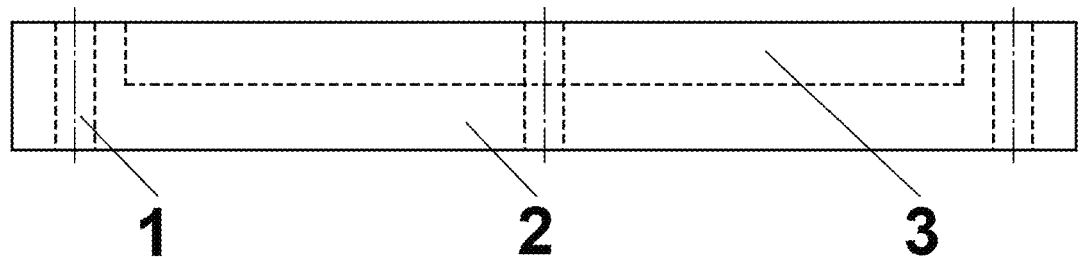
FIG. 1 is a front view of a sheet clamping tooling.

In the drawings: 1 through hole; 2 metal cover plate; 3 groove; 4 fastening bolt; 5 metal sheet; 6 substrate; and 7 microneedle body.

DETAILED DESCRIPTION

The technical solution of the present invention is described below in detail with reference to drawings. The embodiments of the present invention are only used for describing and explaining the technical solution of the present invention rather than limitation. Although the present invention is described in detail with reference to the preferred embodiments, those ordinary skilled in the art shall understand that the technical solution of the present invention can be amended or equivalently replaced without departing from the spirit and the scope of the technical solution of the present invention. The amendment or equivalent replacement shall be covered within the scope of the claims of the present invention.

S1: The microneedle material uses medical 304 stainless steel sheet material with good biocompatibility and excellent strength and toughness. The sheet shown has the sizes of 1000 mm in length, 100 mm in width and 80 microns in thickness. A large-size stainless steel sheet is cut into small metal sheets 5 having proper sizes and convenient for clamping. The metal sheets 5 have length of 50 mm, width of 25 mm and thickness of 80 microns, but not limited to the sizes.

S2: A special sheet clamping tooling is processed.

Figure 2:
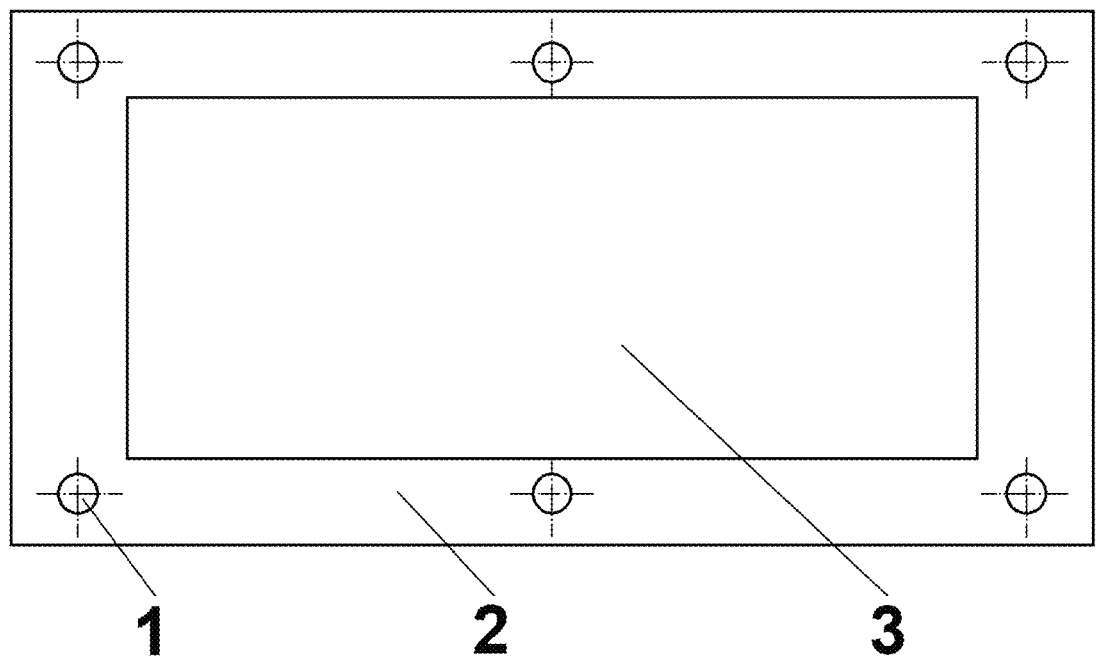
FIG. 2 is a top view of a sheet clamping tooling.
Figure 3:
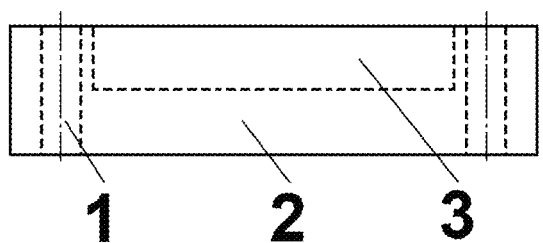
FIG. 3 is a side view of a sheet clamping tooling.

A tooling structure is shown in FIG. 1, FIG. 2 and FIG. 3. The clamping tooling is made of stainless steel which has good electrical conductivity and high strength. The tooling is composed of two identical upper and lower metal cover plates 2. The thickness of each cover plate is 6 mm. Each cover plate has length of 80 mm and width of 55 mm. Inner walls of the upper and the lower cover plates are provided with grooves 3 matched with the sizes of the small metal sheets. The grooves 3 have lengths of 50 mm and widths of 25 mm. The depths of the grooves of the upper and the lower cover plates are 3 mm. Through holes 1 for passing through fastening bolts 4 are processed on both sides of the tooling. In the present embodiment, the through holes 1 have diameter of 6 mm.

Figure 4:
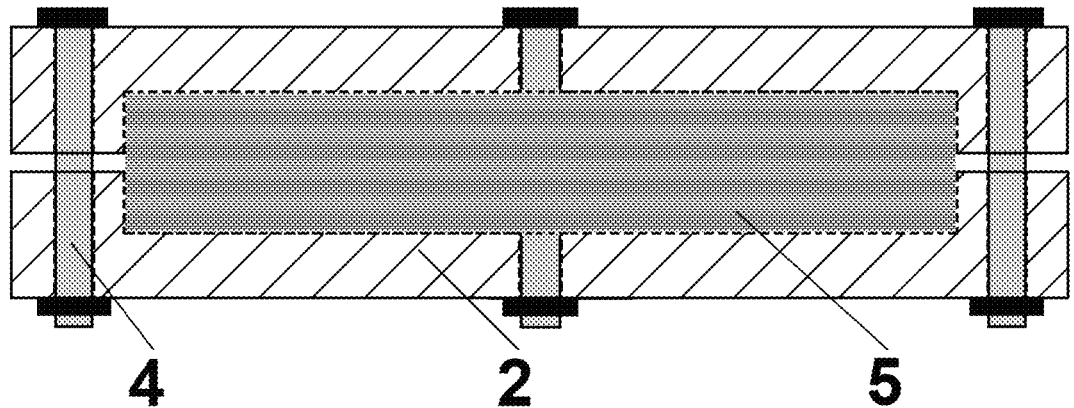
FIG. 4 is a schematic diagram after a metal substrate is placed in a tooling and connected and compacted by a bolt.

S3: 100 small metal sheets 5 (the stacking thickness of the sheets is 8 mm) are placed in the groove 3 of the lower metal cover plate 2; the upper metal cover plate 2 is placed on the cover plate on which the metal sheets are placed, with the groove facing the metal sheets and aligned up and down; and the upper and the lower cover plates are encapsulated by fastening bolts 4, and the metal sheets 5 are compacted. The encapsulated metal sheets and tooling are shown in FIG. 4.

S4: The geometry, size, number, spacing, height and other parameters of the microneedle array are designed as required. The microneedle array is composed of substrates 6 and microneedle bodies 7 which are formed by integrally cutting the same metal sheet 5. In the present embodiment, the height of the microneedle bodies is 300 microns, the width of a root of each microneedle body is 150 microns, the thickness is the thickness of the metal sheet, i.e., 80 micron, and the shapes of the microneedle bodies are ensiform. The number of the microneedles on a single substrate is 7, and a distance is 3.5 mm. A CAD model of the plane microneedles is built according to the geometry and the size of the designed microneedle array.

Figure 5:
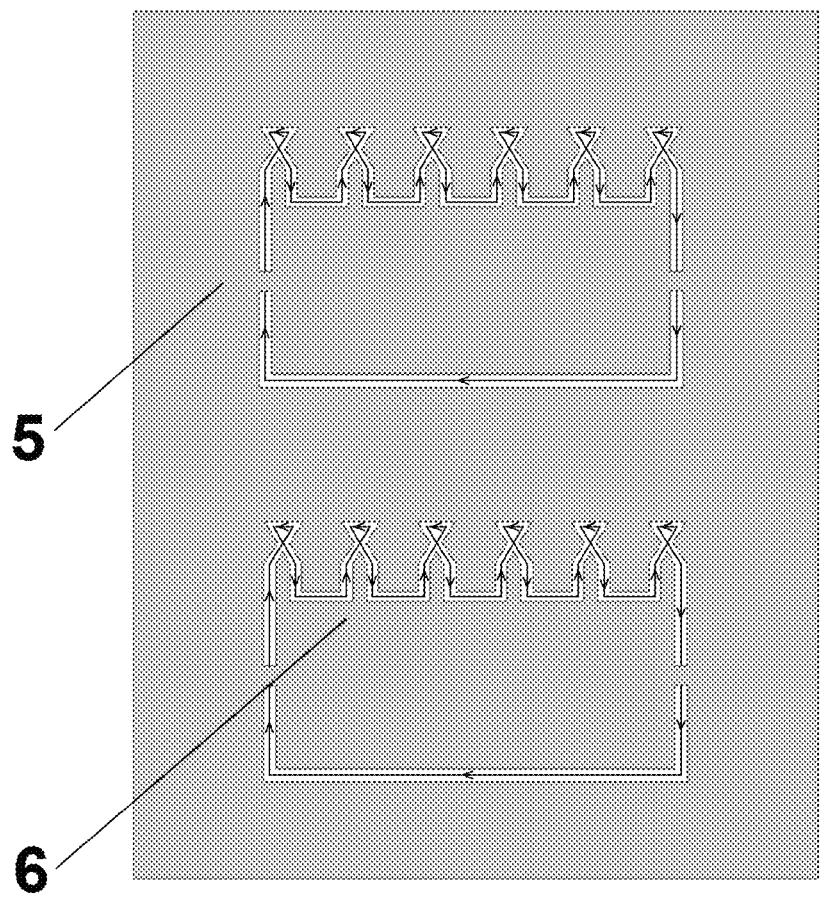
FIG. 5 is a schematic diagram of a wire cutting processing path.
Figure 6:
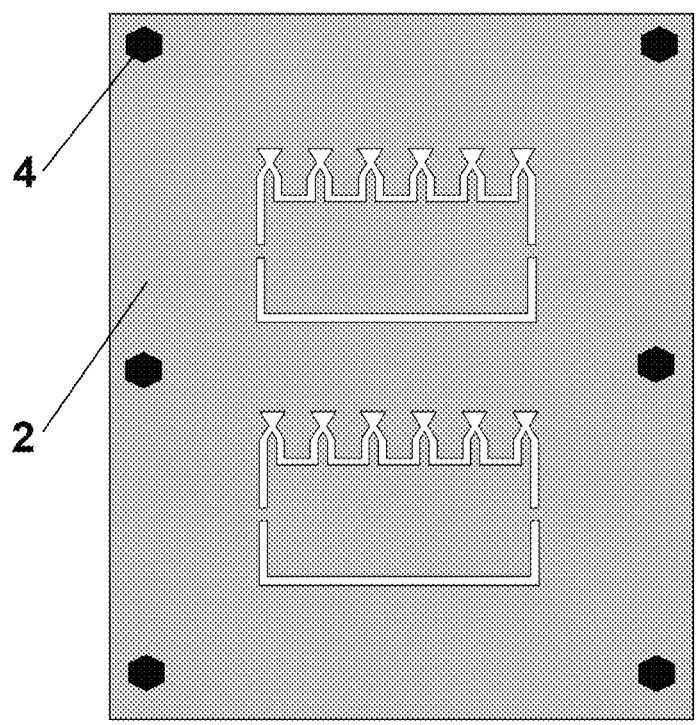
FIG. 6 is a schematic diagram (top view) when a sheet clamping tooling after cut is not disassembled.

S5: The metal sheets and the tooling encapsulated as shown in FIG. 4 as a whole are clamped to a wire cutting device. Cutting process is performed according to a wire path shown in FIG. 5 based on the geometry and the size of the microneedles designed in step S4. Microneedle tips are cut with an "8"-shaped path shown in FIG. 6 to ensure the sharpness of microneedle tips, so as to obtain the tooling and the substrates which are cut, as shown in FIG. 6. In addition, during processing, the substrates are not completely cut, and both sides are reserved for 3 mm without cutting to ensure that the tooling and the metal sheets 5 still form a whole after processing. A schematic diagram (top view) when the metal sheets and the tooling after cut are not disassembled is shown in FIG. 6.

Figure 7:
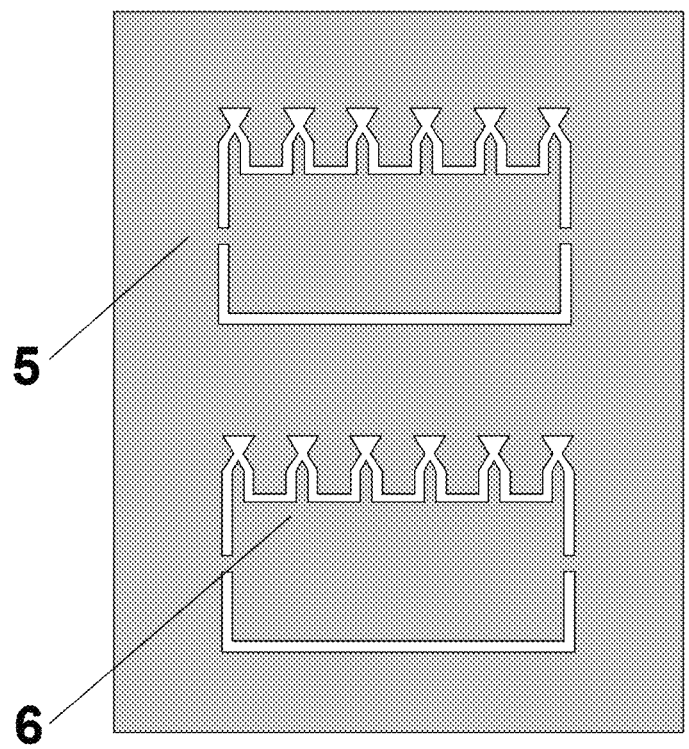
FIG. 7 is an integral schematic diagram of a microneedle array and a substrate after a sheet clamping tooling is disassembled when completing cutting but a metal sheet is not cut.

S6: The fastening bolts 4 on the tooling are taken off, and the processed metal sheets 5 are taken out of the tooling. The metal sheets 5 are placed in a 75% ethanol solution, shaken and washed in an ultrasonic cleaner for 15 minutes, and then baked in a drying cabinet at 120° C. for 2 hours. Finally, the uncut metal sheets 5 shown in FIG. 7 are obtained.

Figure 8:
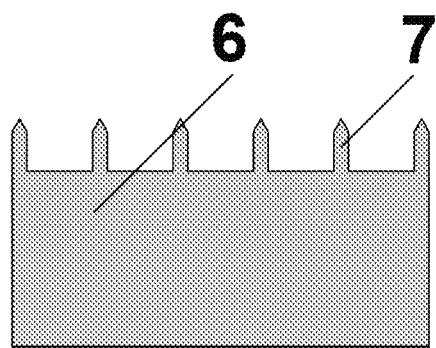
FIG. 8 is a schematic diagram of a sheet plane microneedle array having ensiform needle bodies after final cutting is completed.

S7: A region reserved on both sides of the substrates 6 for 3 mm during processing is cut to separate the sheet microneedle array from the metal sheets 5 to obtain a sheet in-plane metal microneedle array with a plurality of microneedle bodies, as shown in FIG. 8; and the plane microneedle array is further assembled into three-dimensional microneedle arrays with different arrangement specifications for use in design.

The invention claimed is:

1. A manufacturing method for an in-plane metal microneedle array, comprising the following steps:

step 1: cutting a metal sheet into small metal sheets, wherein the thickness of the small metal sheets is 20-200 microns, the length is 30-50 mm, and the width is 10-30 mm;

step 2: processing a special sheet clamping tooling; the tooling is composed of two identical upper and lower metal cover plates, and the overall thickness of each cover plate is 5-10 mm; inner walls of the upper and the lower cover plates of the tooling are processed with grooves matched with the sizes of the small metal sheets to place the metal sheets therein; the depths of the grooves of the upper and the lower cover plates are 1-5 mm; through holes for passing through fastening bolts are processed at edges around the upper and the lower cover plate bodies;

step 3: placing the metal sheets in the groove of the upper or the lower tooling metal cover plate for stacking; adjusting the number of the metal sheets placed at one time according to the thickness of the sheets and the depth of the groove; placing another metal cover plate on the the upper or the lower tooling metal cover plate, with the groove facing the metal sheets and aligned up and down; encapsulating the upper and the lower metal cover plates of the clamping tooling by the fastening bolts, and compacting the metal sheets to form a whole with the upper and the lower cover plates;

step 4: designing the geometry and size of a sheet microneedle array;

the sheet microneedle array is composed of substrates and microneedle bodies; the substrates and the microneedle bodies are formed by integrally cutting the same metal sheet; and the number, shapes and sizes of the microneedle bodies are adjusted as needed;

step 5: clamping the metal sheets and the clamping tooling encapsulated in step 3 to a wire cutting device, determining a wire path according to the microneedle geometry and size designed in step 4 by the wire cutting device, conducting wire cutting on the tooling and the metal sheets as a whole, and processing the metal sheets into the substrates and the microneedle bodies; in the wire cutting process, tips of the microneedle bodies are cut with an "8"-shaped path to ensure the sharpness of the tips of the microneedle bodies; in addition, during wire cutting, both sides of the substrates are reserved for 2 to 5 mm without cutting to ensure that the tooling and the metal sheets still form a whole after cutting;

step 6: taking off the fastening bolts on the tooling, and taking out and washing the processed metal sheets;

step 7: cutting the material on regions reserved on both sides of the substrates on the metal sheets in step 6 to separate the sheet microneedle array from the metal sheets to obtain a sheet in-plane metal microneedle array with a plurality of microneedle bodies.

2. The preparation method for the in-plane metal microneedle array according to claim 1, wherein the clamping tooling is made of stainless steel or 45# steel.

3. The preparation method for the in-plane metal microneedle array according to claim 1, wherein the material of the metal sheets is medical stainless steel or titanium alloy material.

4. An in-plane metal microneedle array prepared by the method of claim 1, wherein the microneedle array is composed of substrates and microneedle bodies; the substrates and the microneedle bodies are in the same plane; a height of each microneedle body is 100-500 microns, a width of a root of each microneedle body is 50-300 microns, and a thickness is the thickness of the metal sheets; the number of the microneedle bodies on each substrate is 3-30, a distance between the microneedle bodies is 0.25-10 mm, and a shape of each microneedle body is triangular or ensiform.

* * * * *